(12) United States Patent
Petasis et al.

(10) Patent No.: US 11,058,659 B2
(45) Date of Patent: Jul. 13, 2021

(54) METHODS AND COMPOSITIONS FOR THE TREATMENT OF OPHALMIC DISEASES AND DISORDERS

(71) Applicant: UNIVERSITY OF SOUTHERN CALIFORNIA, Los Angeles, CA (US)

(72) Inventors: Nicos A. Petasis, Hacienda Heights, CA (US); Mark S. Humayun, Glendale, CA (US); Stan G. Louie, Fullerton, CA (US)

(73) Assignee: University of Southern California, Los Angeles, CA (US)

( * ) Notice: Subject to any disclaimer, the term of this patent is extended or adjusted under 35 U.S.C. 154(b) by 242 days.

(21) Appl. No.: 14/770,073

(22) PCT Filed: Feb. 22, 2014

(86) PCT No.: PCT/US2014/017866
§ 371 (c)(1),
(2) Date: Aug. 24, 2015

(87) PCT Pub. No.: WO2014/130908
PCT Pub. Date: Aug. 28, 2014

(65) Prior Publication Data
US 2016/0000743 A1    Jan. 7, 2016

Related U.S. Application Data

(60) Provisional application No. 61/768,391, filed on Feb. 22, 2013.

(51) Int. Cl.
| | | |
|---|---|---|
| *A61K 31/557* | (2006.01) | |
| *A61P 27/02* | (2006.01) | |
| *A61K 31/216* | (2006.01) | |
| *C07C 69/732* | (2006.01) | |
| *A61K 9/00* | (2006.01) | |

(52) U.S. Cl.
CPC .......... *A61K 31/216* (2013.01); *A61K 9/0048* (2013.01); *C07C 69/732* (2013.01)

(58) Field of Classification Search
CPC ...... A61K 31/216; A61K 31/557; A61P 27/02
See application file for complete search history.

(56) References Cited

U.S. PATENT DOCUMENTS

| | | | |
|---|---|---|---|
| 3,710,795 A | 6/1973 | Higuchi | |
| RE28,819 E | 5/1976 | Thompson | |
| 4,044,126 A | 8/1977 | Cook | |
| 4,328,245 A | 5/1982 | Yu | |
| 4,358,603 A | 11/1982 | Yu | |
| 4,364,923 A | 12/1982 | Cook | |
| 4,409,239 A | 10/1983 | Yu | |
| 4,410,545 A | 10/1983 | Yu | |
| 4,414,209 A | 11/1983 | Cook | |
| 4,522,811 A | 6/1985 | Eppstein | |
| 5,033,252 A | 6/1991 | Carter | |
| 5,052,558 A | 10/1991 | Carter | |
| 5,323,907 A | 6/1994 | Kalvelage | |
| 7,683,193 B2 * | 3/2010 | Petasis | ................... C07C 69/732 554/61 |
| 8,008,282 B2 | 8/2011 | Serhan et al. | |
| 8,034,839 B2 | 10/2011 | Klimko et al. | |
| 8,115,023 B2 | 2/2012 | Petasis | |
| 8,349,896 B2 | 1/2013 | Serhan et al. | |
| 2008/0299130 A1 * | 12/2008 | Ambati | ................... C07K 16/24 424/158.1 |
| 2009/0311201 A1 * | 12/2009 | Van Dyke | ............ A61K 31/202 424/55 |
| 2010/0152290 A1 | 6/2010 | Petasis | |
| 2010/0324138 A1 * | 12/2010 | Bazan | .................. A61K 9/0051 514/560 |
| 2011/0077306 A1 * | 3/2011 | Farjo | .................... A61K 31/122 514/680 |
| 2012/0142772 A1 | 6/2012 | Petasis | |

FOREIGN PATENT DOCUMENTS

| | | |
|---|---|---|
| WO | 0170664 A2 | 9/2001 |
| WO | 2010120719 A1 | 10/2010 |

OTHER PUBLICATIONS

Petasis et al. (Bioorganic & Medicinal Chemistry Letters 18 (2008) 1382-1387).*
International Preliminary Report on Patentability dated Sep. 3, 2015, issued in corresponding International application PCT/US2014/017866.
Extended European Search Report dated Jul. 5, 2016 for corresponding European application 14753828.4 cites the U.S. patent and foreign patent documents.
Petasis et al; "Design and synthesis of benzo-lipoxin A4 analogs with enhanced stability and potent anti-inflammatory properties", Bioorganic & Medicinal Chemistry Letters, Pergamon, Amsterdam, NL, vol. 18, No. 4, Jan. 9, 2008 (Jan. 9, 2008), pp. 1382-1387, XP022479337, ISSN: 0960-894X, DOI: 10.1016/J.JFLUCHEM. 2003.11.029.
Sun Y P et al; "Anti-inflammatory and pro-resolving properties of benzo-lipoxin A4 analogs", Prostaglandins, Leukotrienes and Essential Fatty Acids, Churchill Livingstone, Edinburgh, vol. 81, No. 5-6, Nov. 1, 2009 (Nov. 1, 2009), pp. 357-366, XP026775023, ISSN: 0952-3278, DOI: 10.1016/J.PLEFA.2009.09.004 [retrieved on Oct. 22, 2009].

(Continued)

*Primary Examiner* — Jeffrey S Lundgren
*Assistant Examiner* — Chris E Simmons
(74) *Attorney, Agent, or Firm* — McDonnell Boehnen Hulbert & Berghoff LLP

(57) ABSTRACT

This invention provides compounds, methods and compositions for the treatment of ophthalmic diseases and disorders, including retinal and choroidal disorders and related conditions. More particularly, the invention provides a method of using the provided pharmaceutical compositions for the treatment of ophthalmic diseases and disorders, including retinal and choroidal diseases, and related conditions, upon topical administration to the eye.

26 Claims, 10 Drawing Sheets

(56) References Cited

OTHER PUBLICATIONS

R. Medeiros et al; "Molecular Mechanisms of Topical Anti-Inflammatory Effects of Lipoxin A4 in Endotoxin-Induced Uveitis", Molecular Pharmacology, vol. 74, No. 1, Jan. 1, 2008 (Jan. 1, 2008), pp. 154-161, XP055284046, US ISSN: 0026-895X, DOI; 10.1124/mol.108.046870.
Junzo Nokami et al: "Palladium-catalyzed Coupling Reactions of Bromobenzaldohydes with 3,4Di(tert-butyldimenthylsilyioxy)-1-alkene to (3,4-Dihydroxyalkenyl)benzaldehydes in the Synthesis of Lipoxin Analogues", Tetrahedron Letters Pergamon Tetrahedron Letters, Jan. 1, 1998 (Jan. 1, 1998), pp. 1005-1008, XP055284032, Retrieved from the Internet: URL:http://ac.els-cdn.com/S0040403997108012/1-s2.0-S0040403997108012-main.pdf?.
Timothy P. O'Sullivan et al; "Aromatic Lipoxin A 4 and Lipoxin B 4 Analogues Display Potent Biological Activities", Journal of Medicinal Chemistry, vol. 50, No. 24, Nov. 1, 2007 (Nov. 1, 2007), pp. 5894-5902, XP055284051, US ISSN: 0022-2623, DOI: 10.1021/JM060270d.
International Search Report dated May 16, 2014 issued in corresponding PCT application PCT/US2014/017866 cites the U.S. Patents and Publication listed above.

\* cited by examiner

A Treated Week 2

B Treated Week 4

METHODS AND COMPOSITIONS FOR THE TREATMENT OF OPHALMIC DISEASES AND DISORDERS

CROSS-REFERENCE TO RELATED APPLICATIONS

This application is a national stage of international application number PCT/US2014/017866, filed on Feb. 22, 2014 and claims the benefit of U.S. Provisional Application No. 61/768,391, filed Feb. 22, 2013, the entire contents of both of which are incorporated by reference in its entirety.

STATEMENT REGARDING FEDERALLY FUNDED RESEARCH

This invention was made in part with government support under National Institutes of Health Grant No. P50-DE016191. The government has certain rights in the invention.

FIELD OF THE INVENTION

This invention relates to methods and compositions for the treatment of ophthalmic diseases and disorders, including retinal and choroidal disorders and related conditions.

BACKGROUND OF THE INVENTION

Inflammation is initiated as part of the immune response to infection, injury, oxidative stress or other stimuli. Although it begins as a protective and beneficial process, when it does not end properly and/or timely but continues uncontrollably or in an autoimmune manner, it can lead to acute or chronic (persistent) inflammation, which is linked to the pathogenesis of a wide range of diseases affecting a variety of cells, tissues and organs. The list of acute and chronic inflammatory diseases is quite large and includes some of the most common and most challenging or difficult to treat diseases, including major unmet therapeutic needs. Some examples include: cardiovascular disease, arthritis, asthma, acute lung injury, chronic obstructive pulmonary disease, cystic fibrosis, pancreatitis, systemic lupus erythematosus, Sjogren's syndrome, thyroiditis, atherosclerosis, colitis, irritable bowel disease, celiac disease, Crohn's disease, fibromyalgia, nephritis, dermatitis, acne, periodontal disease, sepsis, stroke, Alzheimer's disease, Parkinson's disease, ophthalmic inflammation, retinopathy, retinal edema, uveitis, age-related macular degeneration, diabetes, and cancer.

The treatment of inflammatory diseases typically involves the use of compounds and compositions that inhibit the actions of pro-inflammatory molecules and pathways. Typical approaches include the use of inhibitors of pro-inflammatory enzymes (e.g. COX-1, COX-2); antagonists of pro-inflammatory cytokine receptors or pro-inflammatory chemokine receptors; antagonists of pro-inflammatory lipid receptors (e.g. CysLT1); agonists of glucocorticoid receptors (GR), or antibodies that target pro-inflammatory cytokines (e.g. TNF-alpha, IL-8) or signaling or growth factors (e.g. VEGF). Among these are some of the most widely used anti-inflammatory agents, such as NSAIDS, dexamethasone and other corticosteroids, the small molecule drug singulair, and the antibodies Enbrel and Avastin.

Many diseases of the eye (ophthalmic diseases and disorders) are associated with persistent or chronic inflammation that results in temporary distortion or permanent damage to the site of inflammation. A wide range of ophthalmic diseases and disorders of this type are known for both the front of the eye (e.g. cornea) as well as the back of the eye (e.g. retina, choroid). These ophthalmic diseases and disorders include but are not limited to: diabetic retinopathy, diabetic macular edema, age related macular degeneration, chronic macular edema, retinal vein occlusions, uveitis, posterior non-infectious uveitis, anterior non-infectious uveitis, conjunctivitis, post-operative ocular inflammation, and others.

Each particular disease or disorder is characterized by distinct pathogenesis as a result of persistent or chronic local inflammation. For example, retinal diseases have ischemia and abnormal new vessel growth as their hallmarks. Vascular endothelial growth factor (VEGF), amongst other growth factors, is upregulated as a result of ischemia and/or inflammation and leads to increased retinal vessel permeability, tortuosity, as well as new retinal vessel growth. Increased retinal vessel permeability, in turn, leads to retinal edema and retinal hemorrhages. New vessel growth at the level of the choroid and retina similarly leads to retinal bleeding and even bleeding into the vitreous cavity.

A number of new drugs have been introduced to treat ophthalmic diseases and disorders associated with inflammation. In the case of retinal diseases such as age related macular degeneration, the FDA-approved drugs that are used most frequently are anti-VEGF antibodies such as Bevacizumab (Avastin) or Ranabizumab (Lucentis) that need to be injected monthly into the eye (intravitreally).

However, therapeutics based on antibodies suffer from the drawbacks that they are generally more expensive and have limited routes of administration. Patients may have primary resistance to antibodies, and, over time, some patients may also develop acquired resistance such as in the case of trastuzumab treatment of HER2 positive breast cancer. Therefore, there still exists a need for small molecule therapeutics.

Recent discoveries and investigations on new anti-inflammatory and pro-resolving lipid mediators derived from polyunsaturated fatty acids, including omega-3 fatty acids, suggested a new approach to ending inflammation and promoting resolution. These include the lipoxins, derived from arachidonic acid [Petasis, N. A. et al *Prostaglandins Leukot. Essent. Fatty Acids* 2005, 73, 301-321], as well as the resolvins derived from eicosapentaenoic or docosahexaenoic acid [Serhan, C. N.; Petasis, N. A. *Chem. Rev.* 2011, 111, 5922-5943]. Endogenous molecules of this type, as well as their synthetic structural analogs, were shown to have potent anti-inflammatory and pro-resolving properties that support their potential use for the treatment of inflammatory diseases.

The present invention provides compounds and compositions for the treatment of ophthalmic diseases and disorders. The provided compounds have aromatic rings as a core and mimic the actions of certain anti-inflammatory and pro-resolving lipid mediators. The provided compounds are readily prepared, and have enhanced chemical and biological stability. Some embodiments of the provided compounds have been previously described [Petasis, N. A. et al. *Bioorg. Med. Chem. Lett.* 2008, 18, 1382-1387], and some evidence of anti-inflammatory and pro-resolving actions has been reported [Sun, Y.-P. et al. *Prostagl. Leukot. Essent. Fatty Acids* 2009, 81, 357-366].

The present invention is based on new unexpected findings that demonstrate the ability of the provided compounds to significantly reduce ophthalmic inflammation, as well as ophthalmic angiogenesis and choroidal neovascularization (CNV). The provided compounds are able to reduce endothelial tube formation in vitro (FIG. 1), and have potent actions in several in vivo models of ophthalmic diseases (FIGS. 2-10).

The present invention provides compounds, compositions, and methods of use for the treatment of opthalmic diseases and disorders, including retinal and choroidal disorders, which feature distinct advantages from treatment methods known in the art.

BRIEF SUMMARY OF THE INVENTION

This invention provides compounds, methods and compositions for the treatment of ophthalmic diseases and disorders, including retinal and choroidal disorders and related conditions.

In particular, the invention provides compounds, methods and compositions for the treatment ophthalmic diseases and disorders, including retinal and choroidal disorders and related conditions. Preferred embodiments of the present invention include methods and compositions useful as pharmaceutical compositions for topical administration, periocular and intraocular injection, suprachoroidal microinjection, as well as systemic administration to the eye.

Exemplary compositions generally comprise one or more compounds disclosed herein, either as free carboxylic acid, ester or other carboxyl derivative or a pharmaceutically acceptable salt, and a pharmaceutically acceptable carrier. Exemplary methods generally make use of the provided pharmaceutical compositions for the treatment of ophthalmic diseases and disorders, upon topical administration to the eye.

The provided methods generally make use of the compounds and compositions in treating pathologic conditions caused by inflammatory action. In particular, the invention is suitable for the treatment of diseases of the eye (ophthalmic diseases and disorders) that are associated with persistent or chronic inflammation that results in temporary distortion or permanent damage to the site of inflammation. This includes a wide range of ophthalmic diseases and disorders for both the front of the eye (e.g. cornea) as well as the back of the eye (e.g. retina, choroid). These ophthalmic diseases and disorders include but are not limited to: diabetic retinopathy, diabetic macular edema, age related macular degeneration, chronic macular edema, retinal vein occlusions, uveitis, posterior non-infectious uveitis, anterior non-infectious uveitis, conjunctivitis, and post-operative inflammation.

The provided compounds mimic the actions of anti-inflammatory, pro-resolving, and anti-angiogenic lipid mediators. The prototype molecules are formed in vivo from arachidonic acid, eicosapentaenoic acid or docosahexaenoic acid in the presence or absence of aspirin, and promote the ending of the inflammatory response.

When compositions in accordance with embodiments of the present invention are injected into the eye in the presence of high VEGF, retinal damage, including retinal vascular leakage and the associated retinal edema and hemorrhage may be prevented or mitigated.

Unlike the anti-VEGF antibody drugs currently in use, the present invention discloses the use of small molecule drugs that are able to counter the effects of VEGF and offer multiple advantages in terms of delivery, applicability, and safety. Other aspects and advantages of the present invention will be apparent from the provided drawings and detailed description.

BRIEF DESCRIPTION OF THE DRAWINGS

FIG. 3. Comparison of compound 18 with bevacizumab (Avastin)—Effect on VEGF-induced angiogenesis in a rabbit eye model. The potency of compound 18 was compared with bevacizumab. (A) Study design. Using a VEGF-induction eye model, where 10 µg of VEGF is injected as an intravitreal administration. One dose of 0.5 mg of compound 18 was compared with 1.25 mg bevacizumab after VEGF induction. (B) Results. On Day 3, eyes treated with 0.5 mg of compound 18 had significantly lower retinal edema and angiogenesis as compared to 1.25 mg bevacizumab treatment. On Day 7, retinal edema and angiogenesis between the two treatment groups were similar.

DETAILED DESCRIPTION OF THE INVENTION

A. Definitions

Figure 1:
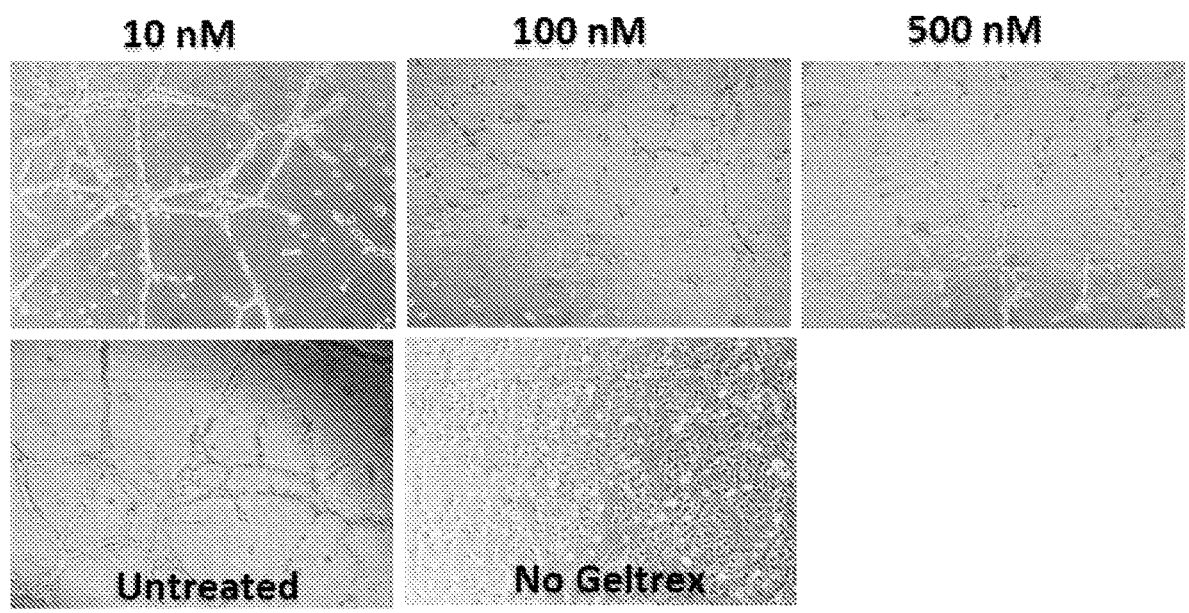
FIG. 1. Inhibition of angiogenesis by compound 18 in a dose-dependent manner—Effect on tube formation. The effect of Compound 18 was evaluated using tube formation assay using a concentration escalation design. At greater than 100 nM demonstrated notable inhibition of tube formation when compared to untreated or no Geltrex. These results were conducted using human mammary endothelial cells (HMEC) cultured in Geltrex, and the formation of tubes were evaluate after 24 hours.

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section will control unless stated otherwise.

As used herein, the nomenclature alkyl, alkoxy, carbonyl, etc. is used as is generally understood by those of skill in the chemical art. As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multicyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals, which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "aryloxy" refers to RO—, in which R is aryl, including lower aryl, such as phenyl.

As used herein, "acyl" refers to a —COR group, including for example alkylcarbonyl, cycloalkylcarbonyl, arylcarbonyl, or heteroarylcarbonyls, all of which may be optionally substituted.

As used herein "subject" is an animal, typically a mammal, including human, such as a patient.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, the term "treatment" means any manner in which one or more of the symptoms of a disease or disorder are ameliorated or otherwise beneficially altered. Treatment also encompasses any pharmaceutical use of the compositions herein, such as use for treating an ophthalmic disease.

As used herein, amelioration of the symptoms of a particular disorder by administration of a particular compound or pharmaceutical composition refers to any lessening, whether permanent or temporary, lasting or transient that can be attributed to or associated with administration of the composition.

B. Compounds

As set forth above, this invention provides compounds, methods and compositions for the treatment of ophthalmic diseases and disorders, including retinal and choroidal diseases, and related conditions.

Compounds in accordance with embodiments of the present invention will have the common property of being structural analogs of natural anti-inflammatory and pro-resolving lipid mediator compounds, including but not limited to the lipoxins or aspirin-triggered lipoxins (e.g. lipoxin $A_4$, lipoxin $B_4$, 15-epi-lipoxin $A_4$, 15-epi-lipoxin $B_4$) or the resolvins or aspirin-triggered resolvins (e.g. resolvin E1, resolvin D1, resolvin D2) and other related lipid mediators derived from polyunsaturated fatty acids (e.g. arachidonic acid, eicosapentaenoic acid or docosahexaenoic acid).

In one exemplary embodiment, there is provided compounds having the general formula 1, and composition comprising one or more said compounds:

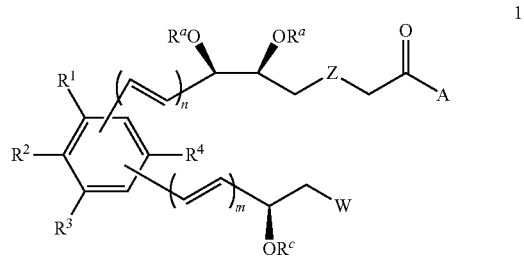

wherein:
A is hydroxy, alkoxy, aryloxy, amino, alkylamino, dialkylamino or a salt —OM, where M is a cation selected from the group consisting of ammonium, tetra-alkyl ammonium, and the cations of sodium, potassium, magnesium and zinc;

Z is $CH_2$, $CH_2CH_2$, CH=CHCH$_2$, CH=CHCH$_2CH_2$, or $OCH_2$

W is hydrogen, alkyl, alkenyl, alkynyl, aryl, heteroaryl, halo, hydroxy, alkoxy, aryloxy, carboxy, amino, alkylamino, dialkylamino, acylamino, or carboxamido;

$R^a$, $R^b$ and $R^c$ are independently selected from a group costing of hydrogen, alkyl, aryl, acyl or alkoxyacyl;

$R^1$, $R^2$, $R^3$ and $R^4$ are independently selected from a group costing of hydrogen, alkyl, alkenyl, alkynyl, aryl, heteroaryl, halo, hydroxy, alkoxy, aryloxy, acyl, carboxy, amino, alkylamino, dialkylamino, acylamino, or carboxamido;

the integer n is zero, one or two;

the integer m is zero, one or two; and the substituents to the aromatic ring are attached either ortho, meta or para.

In another preferred embodiment, there is provided compounds having a general formula according to 2, 3 or 4, and compositions comprising one or more said compound(s):

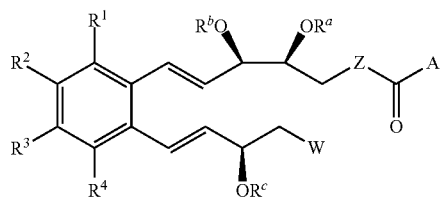

2

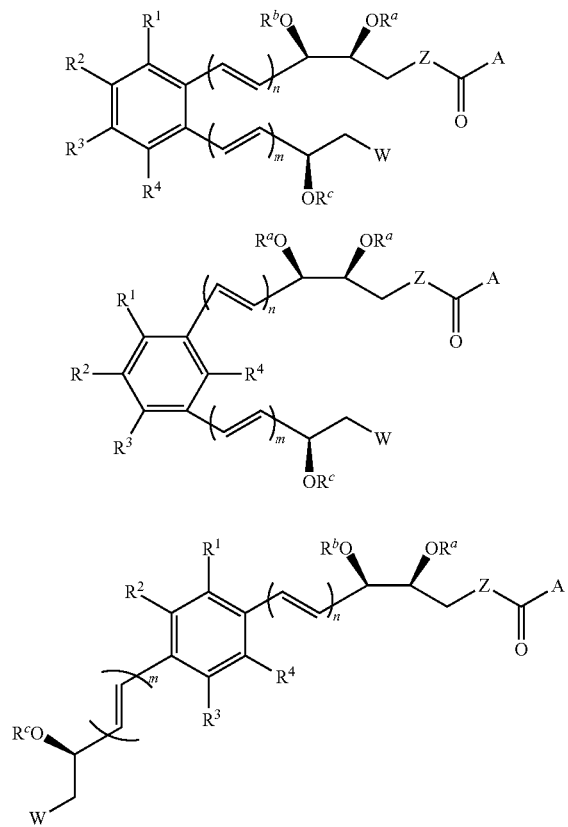

3

4 wherein:
  A is hydroxy, alkoxy, aryloxy, amino, alkylamino, dialkylamino or a salt —OM, where M is a cation selected from the group consisting of ammonium, tetra-alkyl ammonium, and the cations of sodium, potassium, magnesium and zinc;
  Z is $CH_2$, $CH_2CH_2$, $CH{=}CHCH_2$, $CH{=}CHCH_2CH_2$, or $OCH_2$
  W is hydrogen, alkyl, alkenyl, alkynyl, aryl, heteroaryl, halo, hydroxy, alkoxy, aryloxy, carboxy, amino, alkylamino, dialkylamino, acylamino, or carboxamido;
  $R^a$, $R^b$ and $R^c$ are independently selected from a group costing of hydrogen, alkyl, aryl, acyl or alkoxyacyl;
  $R^1$, $R^2$, $R^3$ and $R^4$ are independently selected from a group costing of hydrogen, alkyl, alkenyl, alkynyl, aryl, heteroaryl, halo, hydroxy, alkoxy, aryloxy, acyl, carboxy, amino, alkylamino, dialkylamino, acylamino, or carboxamido;
  the integer n is zero, one or two; and
  the integer m is zero, one or two;

In certain preferred embodiments herein, W is alkyl or aryloxy. In other embodiments, W is butyl. In other embodiments, W is p-fluorophenoxy. In certain embodiments herein, A is hydroxy or alkoxy. In certain preferred embodiments Z is $CH_2CH_2$ or $OCH_2$. In certain embodiments herein, Z is $CH{=}CHCH_2CH_2$.

In another preferred embodiment, there is provided compounds having the general structure 5, and compositions comprising one or more said compound(s):

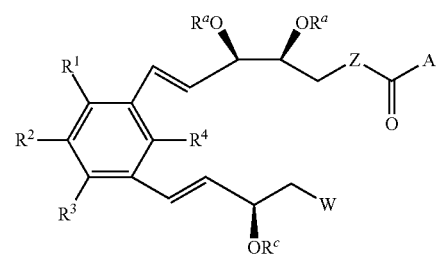

5 wherein:
  A is hydroxy, alkoxy, aryloxy, amino, alkylamino, dialkylamino or a salt —OM, where M is a cation selected from the group consisting of ammonium, tetra-alkyl ammonium, and the cations of sodium, potassium, magnesium and zinc;
  Z is $CH_2$, $CH_2CH_2$, $CH{=}CHCH_2$, $CH{=}CHCH_2CH_2$, or $OCH_2$
  W is hydrogen, alkyl, alkenyl, alkynyl, aryl, heteroaryl, halo, hydroxy, alkoxy, aryloxy, carboxy, amino, alkylamino, dialkylamino, acylamino, or carboxamido;
  $R^a$, $R^b$ and $R^c$ are independently selected from a group costing of hydrogen, alkyl, aryl, acyl or alkoxyacyl; and
  $R^1$, $R^2$, $R^3$ and $R^4$ are independently selected from a group costing of hydrogen, alkyl, alkenyl, alkynyl, aryl, heteroaryl, halo, hydroxy, alkoxy, aryloxy, acyl, carboxy, amino, alkylamino, dialkylamino, acylamino, or carboxamido.

In yet another preferred embodiment, there is provided compounds having the general structure 6, and compositions comprising one or more said compound(s):

6 wherein:
  A is hydroxy, alkoxy, aryloxy, amino, alkylamino, dialkylamino or a salt —OM, where M is a cation selected from the group consisting of ammonium, tetra-alkyl ammonium, and the cations of sodium, potassium, magnesium and zinc;
  Z is $CH_2$, $CH_2CH_2$, $CH{=}CHCH_2$, $CH{=}CHCH_2CH_2$, or $OCH_2$
  W is hydrogen, alkyl, alkenyl, alkynyl, aryl, heteroaryl, halo, hydroxy, alkoxy, aryloxy, carboxy, amino, alkylamino, dialkylamino, acylamino, or carboxamido;
  $R^a$, $R^b$ and $R^c$ are independently selected from a group costing of hydrogen, alkyl, aryl, acyl or alkoxyacyl; and
  $R^1$, $R^2$, $R^3$ and $R^4$ are independently selected from a group costing of hydrogen, alkyl, alkenyl, alkynyl, aryl, heteroaryl, halo, hydroxy, alkoxy, aryloxy, acyl, carboxy, amino, alkylamino, dialkylamino, acylamino, or carboxamido.

In another preferred embodiment, there is provided compounds having the general structure 7, and compositions comprising one or more said compound(s):

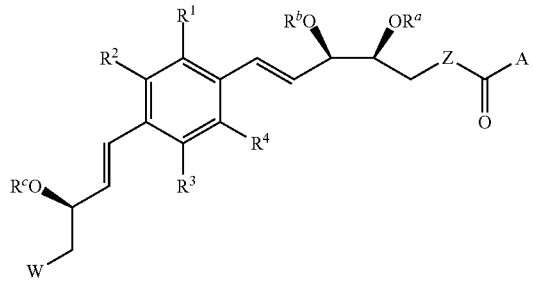

7 wherein:
- A is hydroxy, alkoxy, aryloxy, amino, alkylamino, dialkylamino or a salt —OM, where M is a cation selected from the group consisting of ammonium, tetra-alkyl ammonium, and the cations of sodium, potassium, magnesium and zinc;
- Z is $CH_2$, $CH_2CH_2$, $CH=CHCH_2$, $CH=CHCH_2CH_2$, or $OCH_2$
- W is hydrogen, alkyl, alkenyl, alkynyl, aryl, heteroaryl, halo, hydroxy, alkoxy, aryloxy, carboxy, amino, alkylamino, dialkylamino, acylamino, or carboxamido;
- $R^a$, $R^b$ and $R^c$ are independently selected from a group costing of hydrogen, alkyl, aryl, acyl or alkoxyacyl; and
- $R^1$, $R^2$, $R^3$ and $R^4$ are independently selected from a group costing of hydrogen, alkyl, alkenyl, alkynyl, aryl, heteroaryl, halo, hydroxy, alkoxy, aryloxy, acyl, carboxy, amino, alkylamino, dialkylamino, acylamino, or carboxamido.

In still some other preferred embodiments, there are provided compounds having the general structures 8, 9 or 10, and compositions comprising one or more said compound(s):

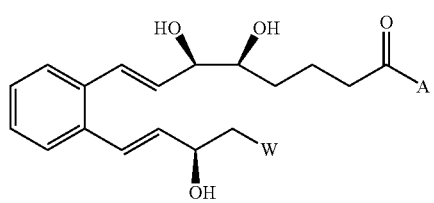

8

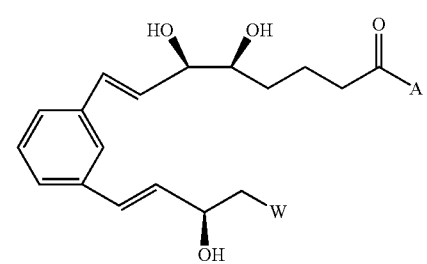

9

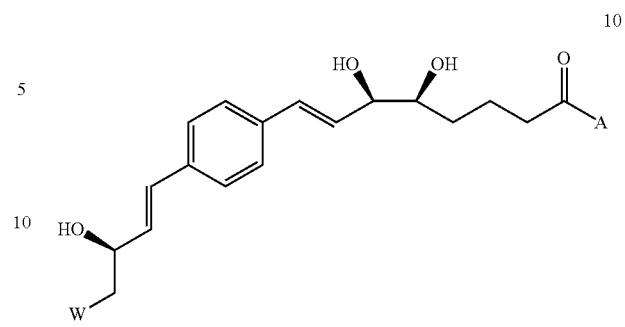

10 wherein:
- A is hydroxy, alkoxy, aryloxy, amino, alkylamino, dialkylamino or a salt —OM, where M is a cation selected from the group consisting of ammonium, tetra-alkyl ammonium, and the cations of sodium, potassium, magnesium and zinc; and
- W is hydrogen, alkyl, alkenyl, alkynyl, aryl, heteroaryl, halo, hydroxy, alkoxy, aryloxy, carboxy, amino, alkylamino, dialkylamino, acylamino, or carboxamido.

In some preferred embodiments, the provided compounds are selected from the list of compounds 11, 12, 13 or 14:

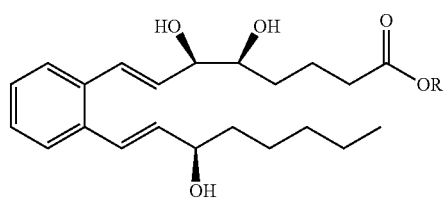

11

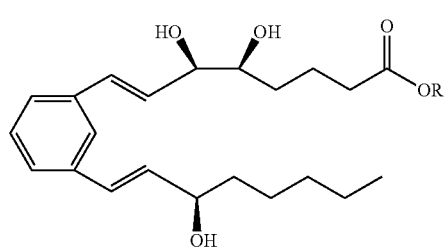

12

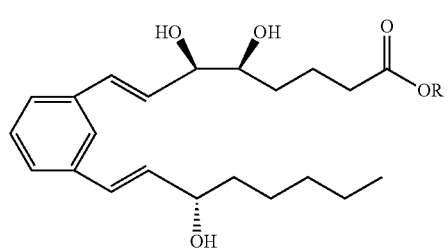

13

14

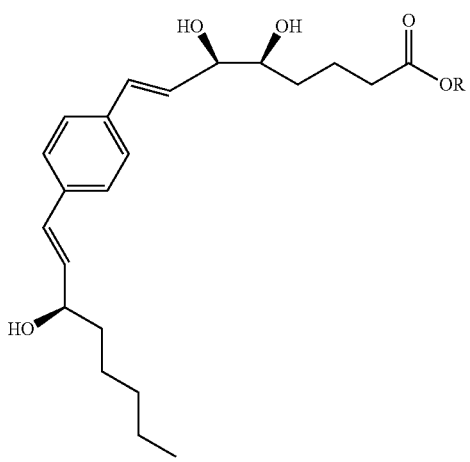

wherein:
wherein R is hydrogen, methyl, ethyl, alkyl, cycloalkyl, arylalkyl, a salt —OM, where M is a cation selected from the group consisting of ammonium, tetra-alkyl ammonium, and the cations of sodium, potassium, magnesium and zinc, or R is attached to a polymeric material or nanoparticle.

C. Preparation of the Compounds

The compounds provided herein may be prepared by methods known in the art or by the general methods described herein. A common theme in the synthetic approach to these compounds is the use of iterative metal-mediated couplings of suitable intermediates, using well-known cross-coupling methods including but not limited to Suzuki coupling and Heck coupling.

In certain embodiments, compounds of the general formula 1 can be prepared according to Scheme 1.

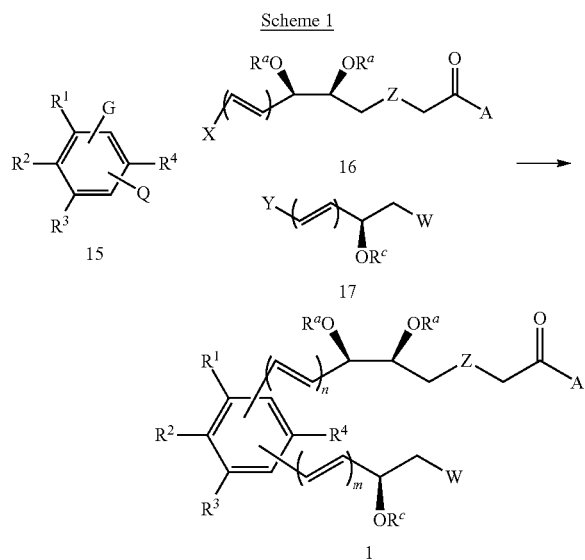

wherein:
G, Q, X and Y are independently selected from a group consisting of bromo, chloro, iodo, triflyl, diazonium, iodonium, boronic acid, boronate, borinate, borate, trifluoroborate, stannyl, perfluorostannyl, silyl, zinc, magnesium or copper.

Compound 15 is first reacted with either 16 or 17 followed by reaction with the other, in the presence of a Pd, Ni or Cu catalyst, provided that in each case appropriate combinations of G, Q, X and Y are present in the reacting compounds.

Appropriate reaction combinations among 15+16 or 15+17 involve the combination of compound 15 having G or C selected from a group consisting of: bromo, chloro, iodo, triflyl, diazonium, iodonium and a compound 16 or 17 having X and Y independently selected from a group consisting of boronate, borinate, borate, trifluoroborate, stannyl, perfluorostannyl, silyl, zinc, magnesium or copper.

The coupling reactions among 15, 16 and 17 can also be carried out in sequence or in one pot. In particular embodiments, compounds 15, 16 and 17 can also be connected to a polymeric chain or other solid phase material.

D. Formulation of Pharmaceutical Compositions

The pharmaceutical compositions provided herein contain therapeutically effective amounts of one or more of compounds provided herein in a pharmaceutically acceptable carrier.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of conditions including, but not limited to, undesired cell proliferation, coronary restenosis, osteoporosis and syndromes characterized by chronic inflammation, autoimmune diseases and cardiovascular diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated undesired cell proliferation, coronary restenosis, osteoporosis, syndromes characterized by chronic inflammation, autoimmune diseases and cardiovascular diseases as described herein.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions.

Compounds are included in an amount effective for ameliorating one or more symptoms of, or for treating or preventing diseases or disorders associated with undesired cell proliferation, coronary restenosis, osteoporosis, syndromes characterized by chronic inflammation, autoimmune diseases and cardiovascular diseases as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, hydroxyethyl cellulose (HEC), β-cyclodextin, hydroxypropyl β-cyclodextrin, carboxymethyl cellulose colloidal solutions, hydroxyethyl cellulose colloidal solutions polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In another embodiment, the bioactive lipid(s) are administered in a polymer formulation, including but not limited to Poly-D,L-Lactic-Co-Glycolic Acid (PLGA), poly-lactic acid (PLA), PLA-PLGA co-polymers, polycaprolactone particles, and chitosan nanoparticles.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical compositions of the present invention may be advantageously provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain, along with the active ingredient, a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time-release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with undesired cell proliferation, coronary restenosis, osteoporosis, syndromes characterized by chronic inflammation, autoimmune diseases and cardiovascular diseases. It is to be understood that such combination therapy constitutes a further aspect of the compositions and methods of treatment provided herein.

1. Compositions for Oral Administration

Oral pharmaceutical dosage forms are solid, gel or liquid. The solid dosage forms are tablets, capsules, granules, and bulk powders. Types of oral tablets include compressed, chewable lozenges and tablets that may be enteric-coated, sugar-coated or film-coated. Capsules may be hard or soft gelatin capsules, while granules and powders may be provided in non effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds, which produce a pleasant, taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603 (the relevant portions thereof are incorporated herein by reference). Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate-controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Formulations contemplated herein also include lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient, which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma, the relevant portions thereof are incorporated herein by reference). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives thereof can be packaged as articles of manufacture containing packaging material, a compound or pharmaceutically acceptable derivative thereof provided herein, which is used for treatment, prevention or amelioration of one or more symptoms associated with undesired cell proliferation, coronary restenosis, osteoporosis, syndromes characterized by chronic inflammation, autoimmune diseases and cardiovascular diseases condition, and a label that indicates that the compound or pharmaceutically acceptable derivative thereof is used for treatment, prevention or amelioration of one or more symptoms associated with undesired cell proliferation, coronary restenosis, osteoporosis, syndromes characterized by chronic inflammation, autoimmune diseases and cardiovascular diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252 (the relevant portions thereof are incorporated herein by reference). Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder associated with undesired cell proliferation, coronary restenosis, osteoporosis, syndromes characterized by chronic inflammation, autoimmune diseases and cardiovascular diseases condition.

E. Methods of Use of the Compounds and Compositions

Compounds of the invention are structural analogs of naturally-occurring molecules that are known to have biological activity against a wide variety of targets, including diseases or conditions associated with inflammation or inflammatory response, undesired cell proliferation, such as cancer, and cardiovascular diseases. As such, the compounds of the invention are expected to have similar activity against those targets.

Accordingly, in one aspect, the invention features methods of ameliorating or treating diseases or conditions associated with inflammation or inflammatory response, involving the administration to a subject of a therapeutically effective amount of a compound or compounds of the invention, such that inflammation or an inflammatory response are significantly reduced or eliminated in the subject. A significant reduction includes the reduction or elimination of a symptom or symptoms associated with the inflammation or inflammatory response.

In another aspect, the invention features methods of ameliorating or treating diseases or conditions associated with undesired cell proliferation, such as cancer, involving the administration to a subject of an effective amount of a compound or compounds of the invention. In general, an effective amount is an amount sufficient to ensure adequate exposure of a target cell population, such that abnormal cell proliferation is substantially slowed or halted. A target population is a population of cells undergoing abnormal cell proliferation, such as cancerous and/or tumorous growth.

In one exemplary embodiment, the invention provides methods and compositions for the treatment of ophthalmic diseases and disorders, including retinal and choroidal disorders and related conditions, comprising the timely topical administration of a provided compound or pharmaceutical composition.

In a preferred embodiment, the invention provides a method for the treatment of ophthalmic diseases and disorders, including retinal and choroidal disorders and related conditions, comprising the timely local administration of a provided compound or composition during the time course of the disorder.

In a further preferred embodiment, the invention provides a method for the treatment of ophthalmic diseases and disorders, including but not limited to: diabetic retinopathy, age related macular degeneration, chronic macular edema, retinal vein occlusions, posterior non-infectious uveitis, anterior non-inectious uveitis, conjunctivitis, post-operative inflammation, comprising the timely local administration of a provided compound or composition during the time course of the disease or disorder.

In one exemplary embodiment, the invention provides a method for the treatment of ophthalmic diseases and disorders, comprising the timely administration of a provided compound and a pharmaceutically acceptable carrier.

In one embodiment, the invention provides a method for the treatment of ophthalmic diseases and disorders, comprising the timely administration of a combination of a provided compound and an anti-inflammatory or anti-angiogenic agent currently used in the art for the treatment of ophthalmic diseases and disorders.

In one embodiment, the invention provides a method of administration for the provided compounds and compositions, comprising the local administration via intravitreal injection. A method of systemic administration via intravenous injection or via oral formulation is also provided.

In one embodiment, the invention provides a method of administration for the provided compounds and compositions, comprising the local delivery via a slow release method enabled by an implant of a degradable polymeric material containing a provided compound or composition.

In one embodiment, the invention provides a method of administration for the provided compounds and compositions, comprising the local delivery via a slow release enabled by an implanted pump device.

The invention will be further described in the following examples, which are illustrative only, and which are not intended to limit the scope of the invention described in the claims.

EXAMPLES

In the following examples, efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric. Starting materials used in these examples are generally either commercially available or can be readily prepared from commercially available reagents by a procedure involving one or more steps.

Example 1

Effects of Compound 18 in Models of Inflammatory and Angiogenic Ophthalmic Diseases

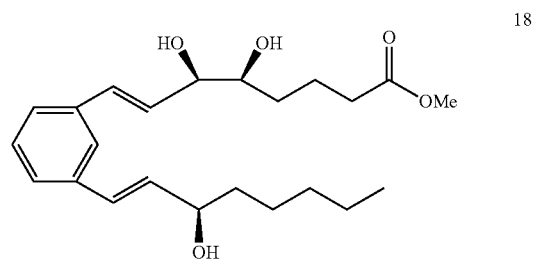 [SMILES: CCCCC[C@@H](O)/C=C/c1cccc(/C=C/[C@@H](O)[C@@H](O)CCCC(=O)OC)c1]

Compound 18 was prepared using methods known in the art. (For example, see U.S. Pat. Nos. 8,115,023, and 7,683,193). Compound 18 exhibited the following activities:

(a) Compound 18 was able to inhibit angiogenesis in a dose-response manner in a tube formation assay (FIG. 1).

Figure 2:
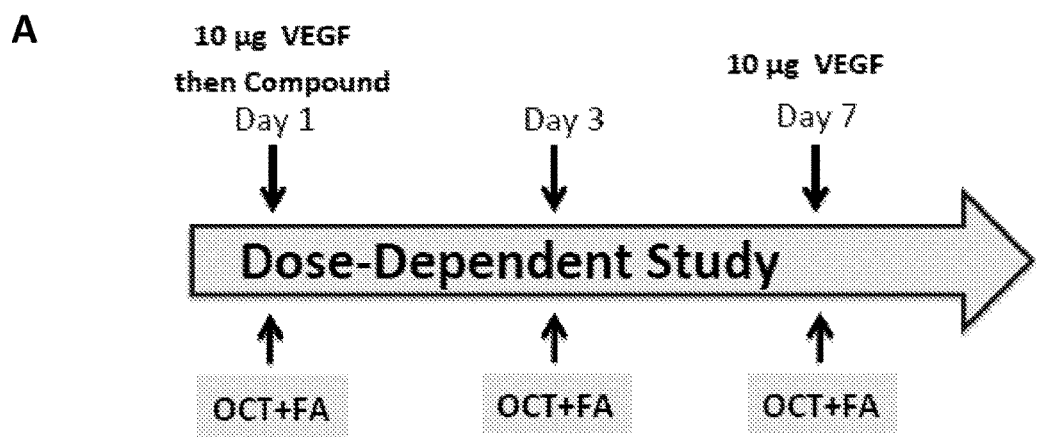
FIG. 2. Inhibition of angiogenesis by compound 18 in a dose-dependent manner—Effect on VEGF-induced angiogenesis in a rabbit eye model. (A) Study design. To evaluate the impact of compound 18, 10 µg of VEGF in each eye is administered as an intravitreal injection. In this study, the activity of compound 18 is evaluated in a concentration escalation manner from 0.125 to 0.5 mg given as a single dosage. A formulation of compound 18 where the dosage is admixed in a total of 50 µL, was administered immediately after VEGF administration. (B) Results. On Day 7, the level of retinal edema and angiogenesis is significantly reduced as compared to vehicle treatment at doses >0.25 mg.
Figure 2:
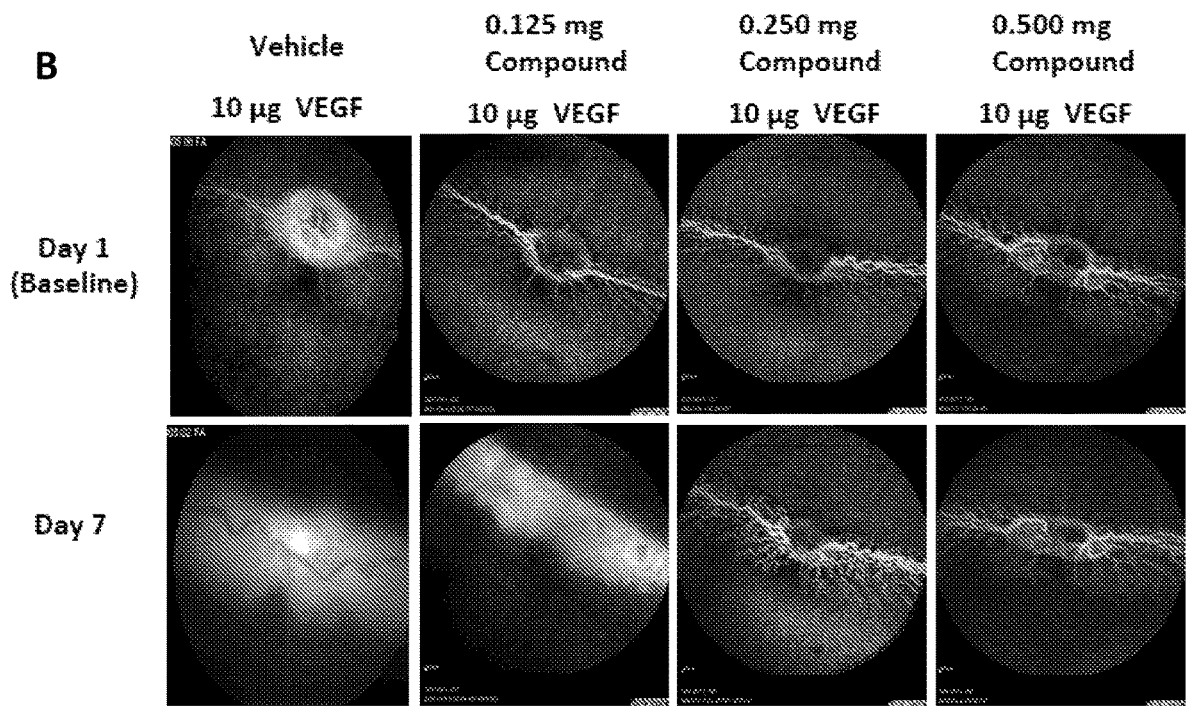

(b) Compound 18 was active in a dose-response manner against the pathological response exhibited in the neovascularization and leakage from a VEGF injection in a VEGF-induced angiogenesis in a rabbit eye model (FIG. 2). On Day 7, the level of retinal edema and angiogenesis is significantly reduced as compared to vehicle treatment.

Figure 3:
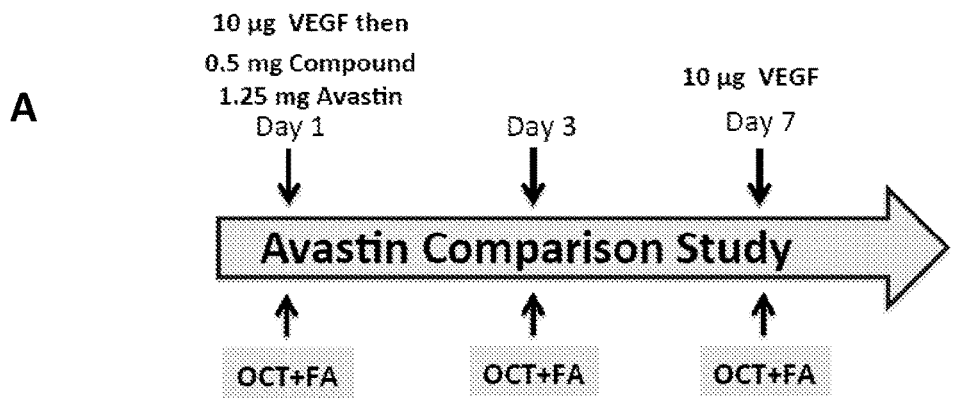
Figure 3:
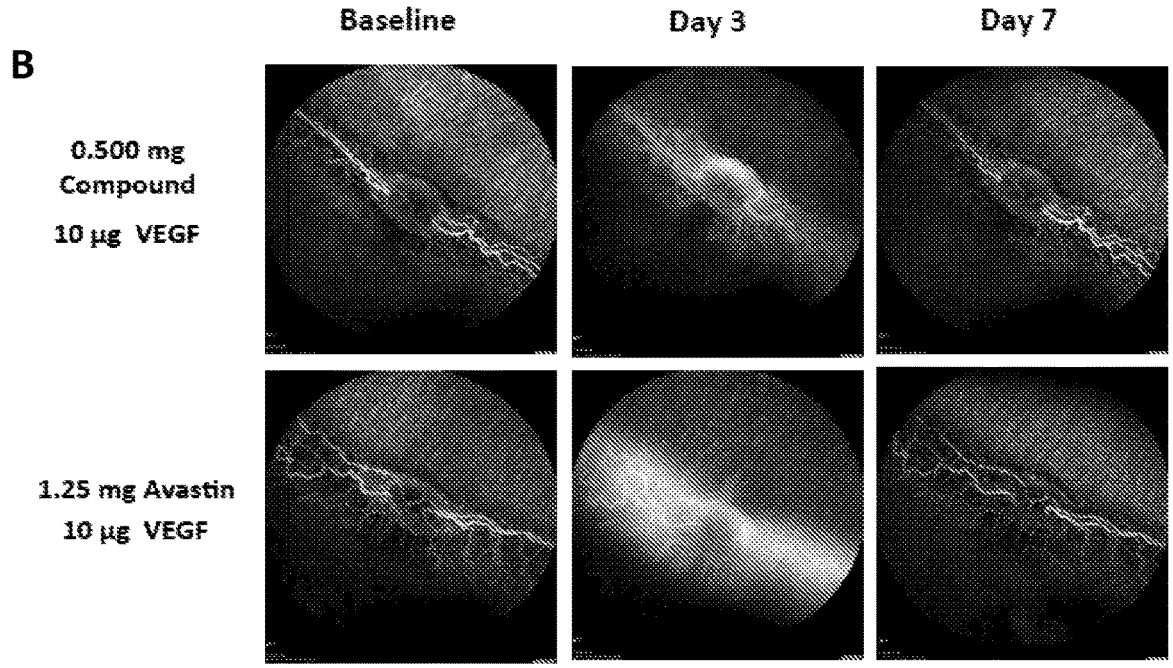
Figure 3:
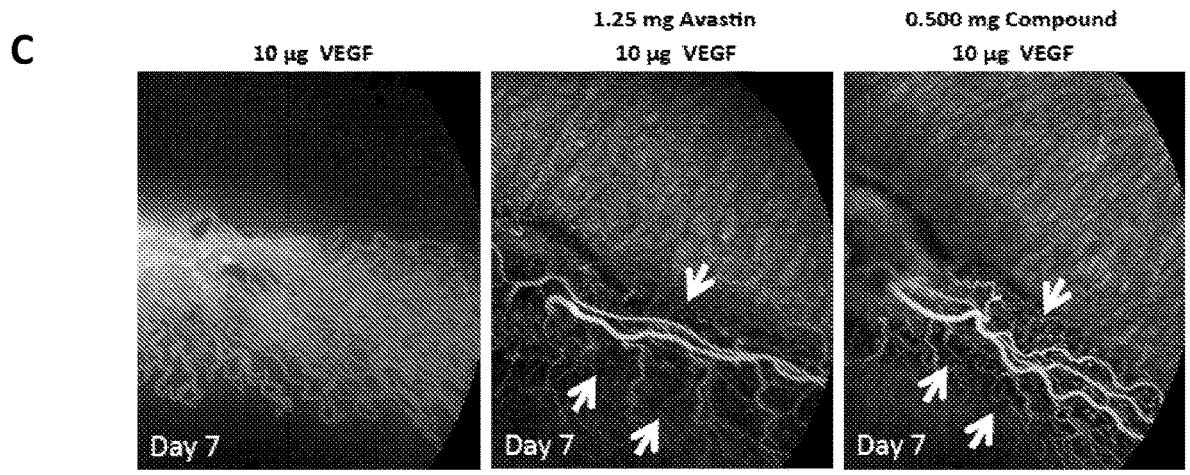

(c) In a VEGF-induced angiogenesis in a rabbit eye model, on Day 3 eyes treated with 0.5 mg of compound 18 had significantly lower retinal edema and angiogenesis as compared to 1.25 mg Avastin treatment. (FIG. 3). On Day 7, retinal edema and angiogenesis between the two treatment groups were similar. This findings shows that compound 18 has comparable or improved activity profile vs Avastin.

Figure 4:
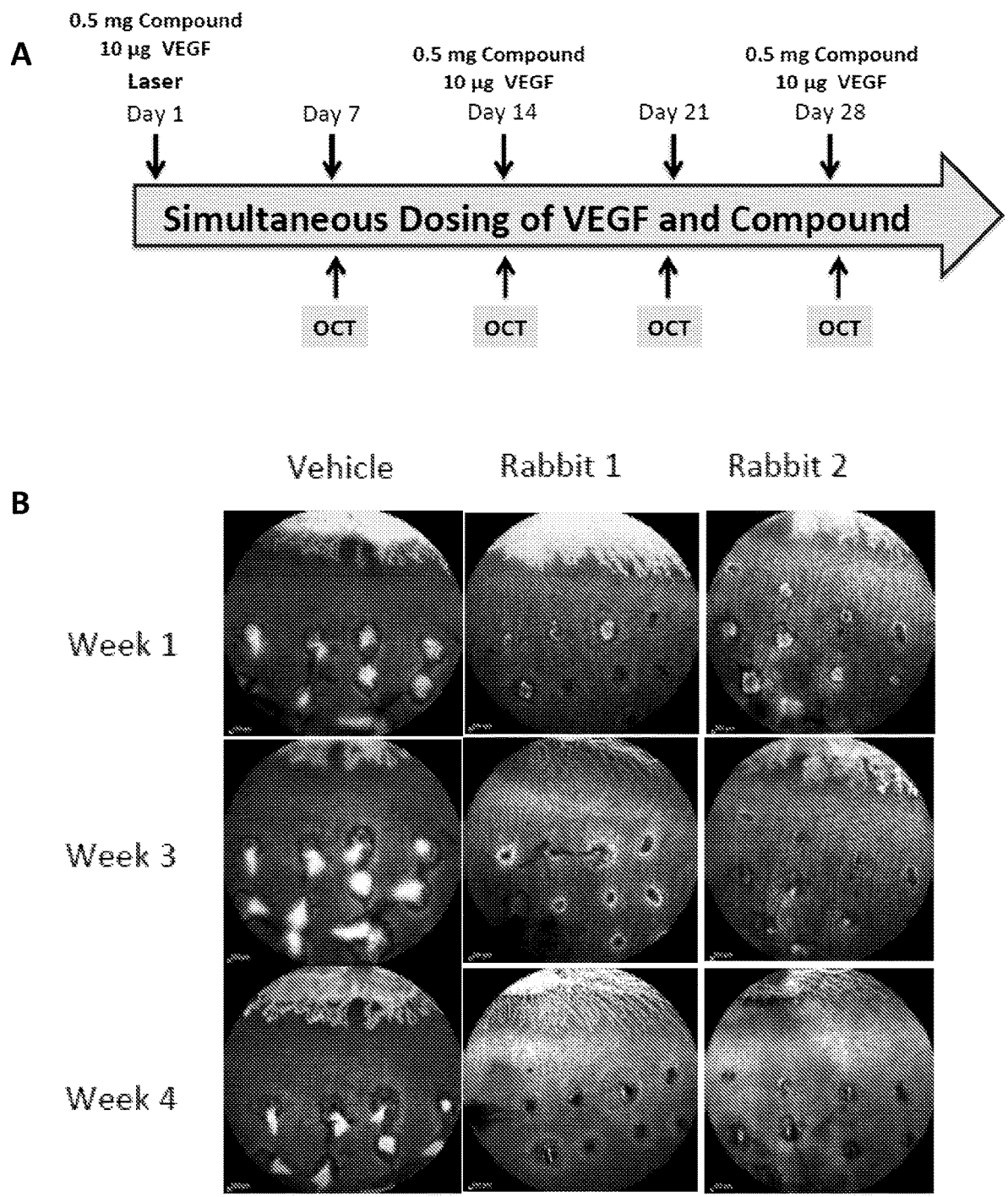
FIG. 4. Effect of compound 18 in a choroidal neovascularization (CNV) model of age-related macular degeneration (AMD). (A) Study Design: Simultaneous treatment model. Choroidal neovascularization (CNV) model, was used to determine its effect on new blood vessel formation. In this figure, laser induced lesions were further supplemented with 10 µg VEGF intravitreal administration every two weeks. Laser induced AMD lesions penetrated the Bruch's membrane. CNV lesions were treated with 0.5 mg compound 18 administered weekly, where first dosage was given at the time of CNV lesion formation. (B) Results. Retinal angiography demonstrates a progressive reduction of retinal edema in the vehicle treated eyes. In contrast, 0.5 mg compound 18 showed a statistically significant reduction in the vessels and edema in the CNV lesions by week 4.

(d) Compound 18 showed potent activity in a simultaneous treatment model of a choroidal neovascularization (CNV) model of age-related macular degeneration (AMD) (FIG. 4). Compound 18 showed a statistically significant reduction in the vessels and edema in the CNV lesions as compared with vehicle.

Figure 5:
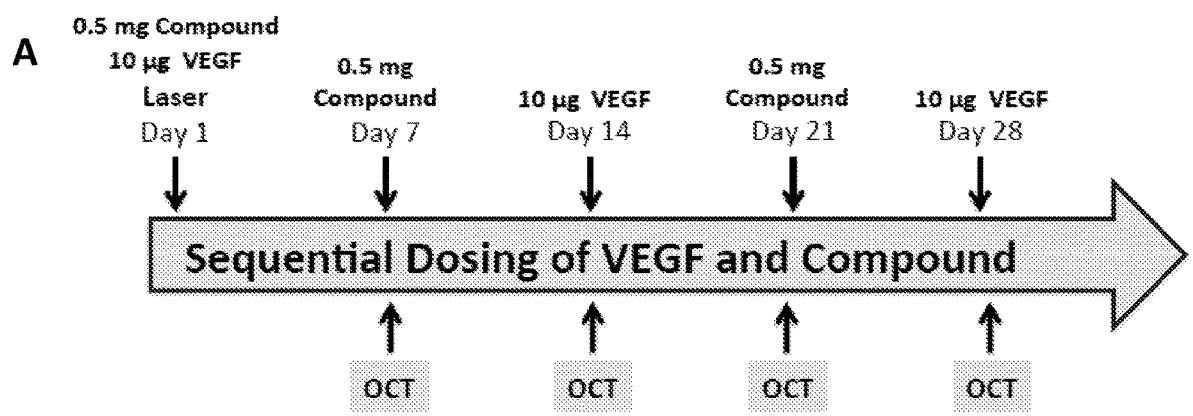
FIG. 5. Effect of compound 18 in a choroidal neovascularization (CNV) model of age-related macular degeneration (AMD) A) Study Design: Sequential treatment model. CNV model was used to determine compound 18's effect on new blood vessel formation. Laser induced lesions were supplemented with 10 µg VEGF intravitreal administration every two weeks. CNV lesions were treated with 0.5 mg compound 18 administered weekly, were given one week after CNV lesion formation. (B) Results. Retinal angiography demonstrates a progressive reduction of retinal edema in the vehicle treated eyes. In contrast, 0.5 mg Compound 18 showed a statistically significant reduction in the vessels and edema in the CNV lesions by week 4.
Figure 5:
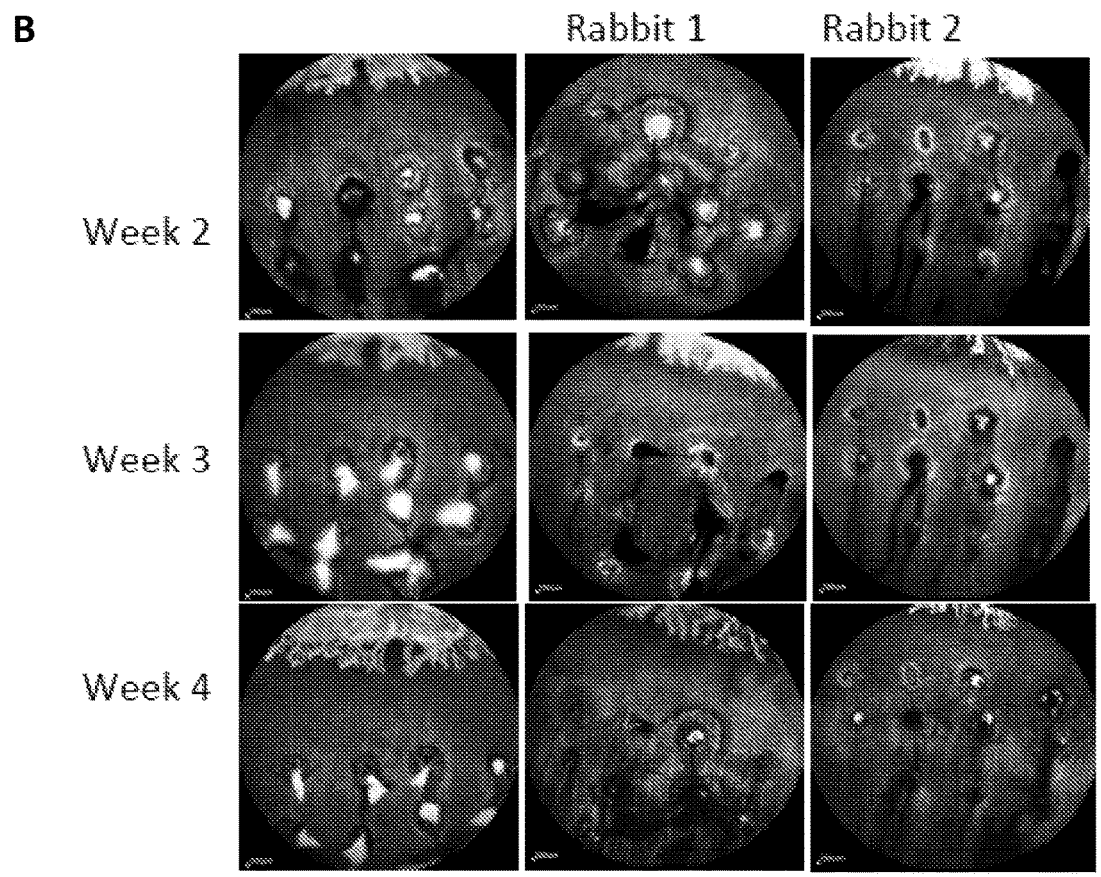

(e) Compound 18 showed potent activity in a sequential treatment model of a choroidal neovascularization (CNV) model of age-related macular degeneration (AMD) (FIG. 5). Compound 18 showed a statistically significant reduction in the vessels and edema in the CNV lesions as compared with vehicle.

Figure 6:
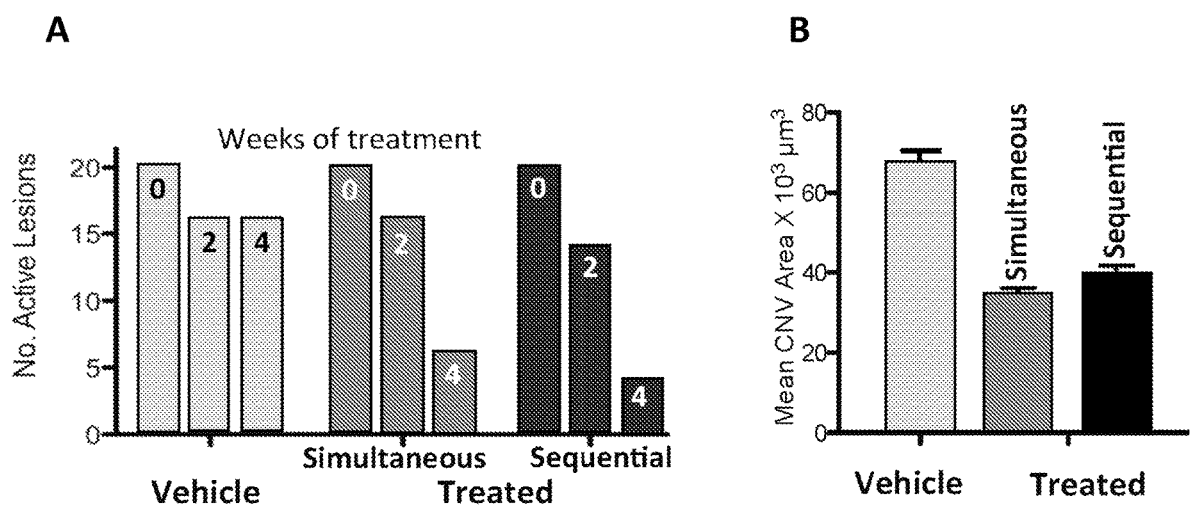
FIG. 6. Quantification of the Lesion Number and Mean Area. CNV lesions were enumerated at baseline, 2 and 4 weeks after CNV lesion formation. (A) Lesion Number. Both groups, sequential (SQ) and simultaneous (SM) treated with compound 18 significantly reduced CNV lesion by week 4 of therapy as compared to vehicle control (Left). (B) Mean Area. The lesions were also measured for their mean CNV area, where both SQ and SM treatment showed a reduction in the mean CNV area (Right).

(f) Quantification of the Lesion Number and Mean Area enumerated at baseline, 2 and 4 weeks after CNV lesion formation showed that both groups, sequential (SQ) and simultaneous (SM) treated with compound 18 significantly reduced CNV lesion by week 4 of therapy as compared to vehicle control (FIG. 6). The lesions were also measured for their mean CNV area, where both SQ and SM treatment showed a reduction in the mean CNV area.

Figure 7:
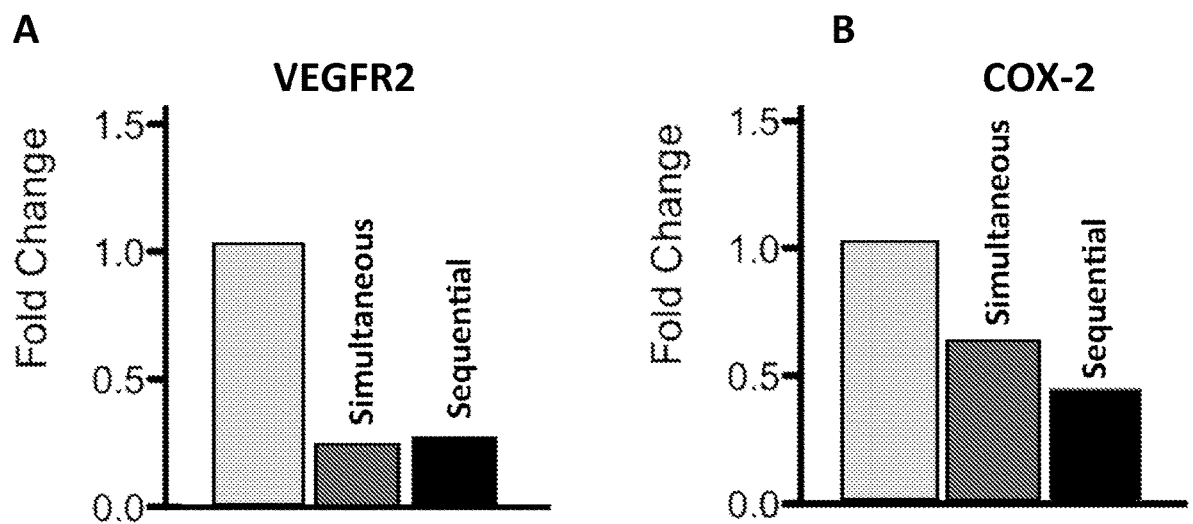
FIG. 7. RT-PCR Data of CNV after treatment. Reduced expression of pro-angiogenic and pro-inflammatory proteins upon treatment with compound 18. Both groups, sequential (SQ) and simultaneous (SM) treated with compound 18 significantly reduced the expression of (A) VEGF receptor 2, and (B) cyclooxygenase-2 (COX-2).

(g) RT-PCR data of CNV lesions after treatment, showed reduced expression of pro-angiogenic and pro-inflammatory proteins upon treatment with compound 18 (FIG. 7). Both groups, sequential (SQ) and simultaneous (SM) treated with compound 18 significantly reduced the expression of VEGF receptor 2, and cyclooxygenase-2 (COX-2).

Figure 8:
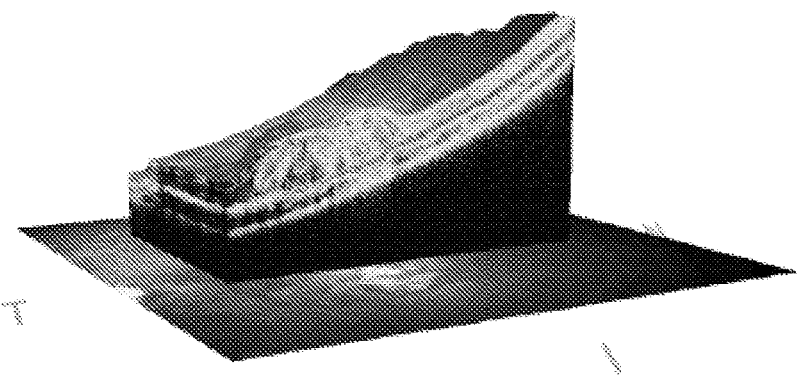
FIG. 8. Optical Coherence Tomography (OCT) of CNV Lesions Over Time. OCT was used to evaluate CNV lesion healing after compound 18 treatment. In this study, compound 18 was able to promote lesion healing at 2 weeks (A) as compared to the same lesion evaluated at 4 weeks (B).
Figure 8:
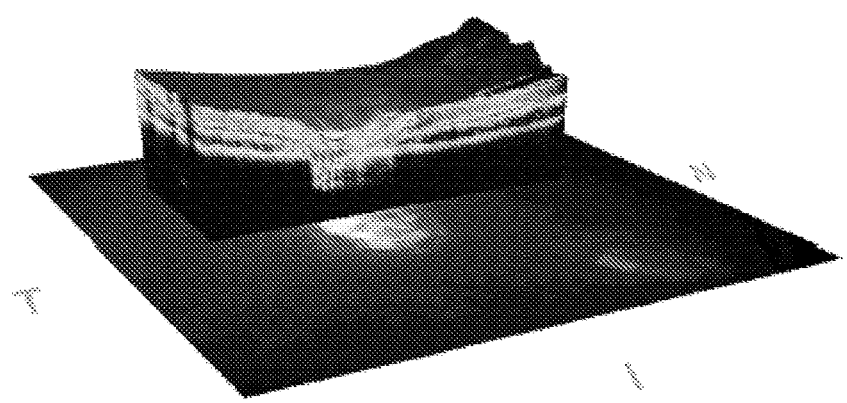

(h) Optical Coherence Tomography (OCT) of CNV Lesions Over Time showed that compound 18 was able to promote healing of a lesion at 4 weeks as compared to the same lesion evaluated at 2 weeks (FIG. 8). Confocal Scanning Fluorescent Microscope of CNV Lesions.

Figure 9:
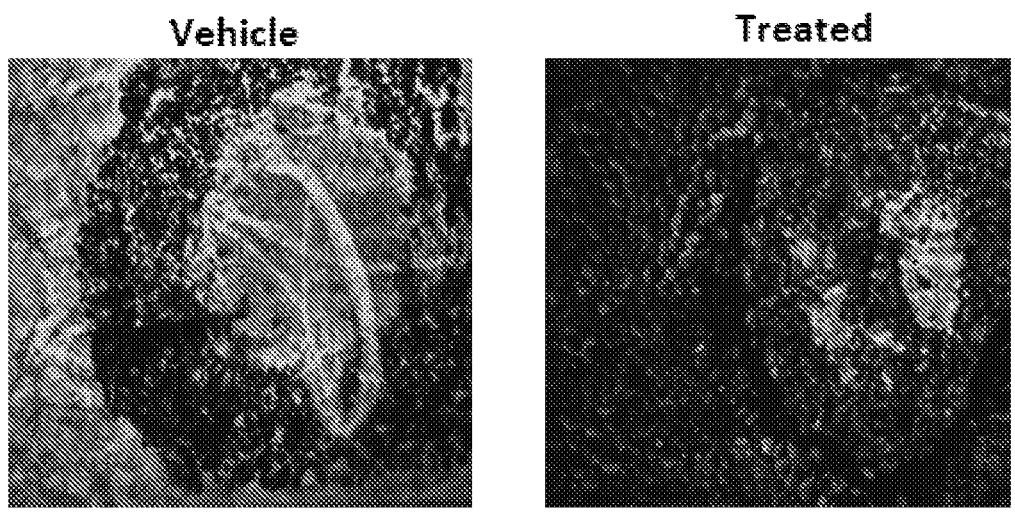
FIG. 9. Confocal Scanning Fluorescent Microscope of CNV Lesions. Confocal scanning fluorescent microscopy is used to visualize the level of neovascular growth. In the vehicle treated lesions (Left), extensive neovascular growth is noted after one month. In contrast, CNV lesions treated with compound 18 a reduction in neovascular growth is noted (Right).

(i) Confocal scanning fluorescent microscopy used to visualize the level of neovascular growth showed that the vehicle treated lesions had extensive neovascular growth after one month. In contrast, CNV lesions treated with compound 18 showed a significant reduction in neovascular growth (FIG. 9).

Figure 10:
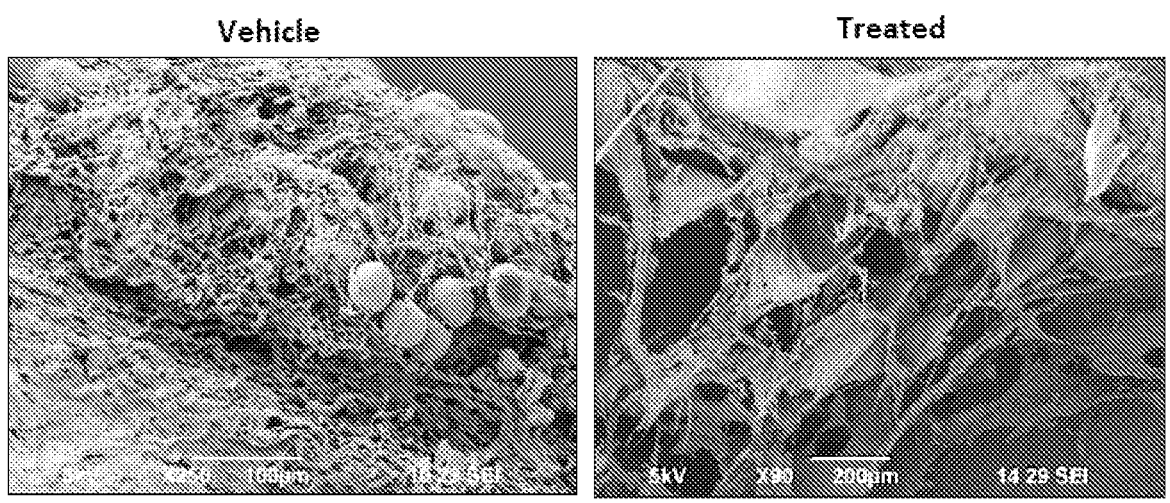
FIG. 10. Confocal Scanning Electron Microscopy of CNV lesions treated with vehicle (Left) was compared with compound 18 treatment (Right). SEM showed neovascular growth penetrating the Bruch's membrane and growing into the subretinal space and into the retinal layers in the eye that was treated with vehicle. In contrast, in eyes that were treated with compound 18 thin-walled fenestrated vascular channels with flat configuration.

(j) Confocal Scanning Electron Microscopy of CNV lesions treated with compound 18 as compared with vehicle SEM showed neovascular growth penetrating the Bruch's membrane and growing into the subretinal space and into the retinal layers in the eye that was treated with vehicle (FIG. 10). In contrast, in eyes that were treated with compound 18 thin-walled fenestrated vascular channels with flat configuration.

These data confirm that compound 18 inhibits angiogenesis and reduces vascular permeability with comparable potency as Avastin. It also reduces the number and size of CNV lesions after 4 weeks of treatment and dramatically reduces neovascular growth in CNV lesions after 4 weeks of treatment. The compound seems to be able to regress the underlying pathogenesis of neovascularization, and it has efficacy for treating ophthalmic diseases and disorders without the usual side effects of NSAIDs and steroids.

Overall, based on its demonstrated properties, compound 18 provides an example of the compounds provided herein and illustrates its potential use for the treatment of inflammatory and angiogenic ophthalmic diseases.

By using methods known to the art, additional modifications of the ester group of compounds that are structurally related to 18 (as defined herein), it is possible to further modify the therapeutic effects of this class of compounds, with the formation of ester groups other than methyl ester, such as alkyl, cycloalkyl, arylalkyl, as well as direct or indirect attachment to polymeric materials or nanoparticles.

What is claimed is:

1. A method for the treatment of a subject with an ophthalmic disease or disorder selected from the group consisting of retinal edema, diabetic retinopathy, diabetic macular edema, chronic macular edema, age related macular degeneration characterized by choroidal neovascularization, retinal vein occlusions, and ophthalmic angiogenesis, the method comprising administering to the subject in need thereof an effective amount of a compound having the structure of formula 12 or 13:

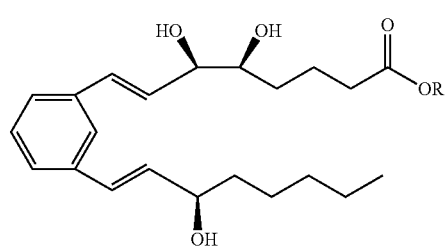

12

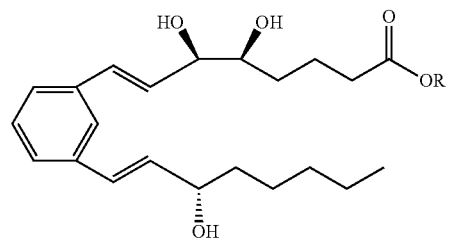

13 wherein R is hydrogen, $C_1$-$C_{15}$ alkyl, or a cation selected from the group consisting of ammonium, tetra-alkyl ammonium, sodium, potassium, magnesium and zinc.

2. The method of claim 1, wherein R is selected from the group consisting of hydrogen, methyl, ethyl, propyl, isopropyl and a cation selected from the group consisting of ammonium, tetra-alkyl ammonium, sodium, potassium, magnesium and zinc.

3. The method of claim 1, wherein the ophthalmic disease or disorder is selected from the group consisting of diabetic retinopathy, diabetic macular edema, chronic macular edema, age related macular degeneration and retinal vein occlusions.

4. The method of claim 1, wherein the compound is administered to the subject by delivery to the eye via at least one of topical administration, periocular and intraocular injection, suprachoroidal microinjection, nanoparticles, polymeric materials, and systemic administration.

5. The method of claim 1, wherein R is ethyl, propyl or isopropyl.

6. The method of claim 1, wherein R is hydrogen.

7. The method of claim 1, wherein R is methyl.

8. The method of claim 1, wherein R is a cation selected from the group consisting of ammonium, tetra-alkyl ammonium, sodium, potassium, magnesium and zinc.

9. The method of claim 1, wherein the compound has the structure of formula 12,

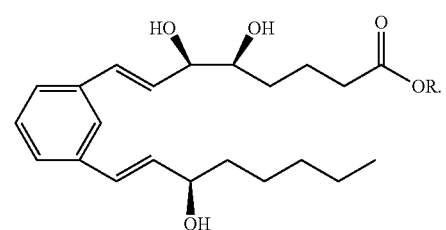

12

10. The method of claim 9, wherein R is methyl.

11. The method of claim 1, wherein the compound has the structure of formula 13,

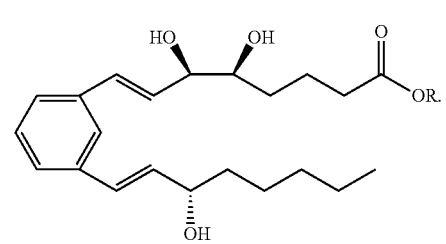

13

12. The method of claim 11, wherein R is methyl.

13. The method of claim 1, wherein the ophthalmic disease or disorder is selected from the group consisting of diabetic retinopathy and diabetic macular edema.

14. The method of claim 1, wherein the ophthalmic disease or disorder is selected from the group consisting of chronic macular edema, age related macular degeneration characterized by choroidal neovascularization, and retinal vein occlusions.

15. The method of claim 1, wherein the ophthalmic disease or disorder is age related macular degeneration characterized by choroidal neovascularization.

16. The method of claim 1, wherein the ophthalmic disease or disorder is retinal edema or ophthalmic angiogenesis.

17. The method of claim 1, wherein the ophthalmic disease is retinal edema.

18. The method of claim 1, wherein the ophthalmic disease is ophthalmic angiogenesis.

19. The method of claim 1, wherein the compound is administered to the subject by delivery to the eye via topical administration, periocular or intraocular injection, suprachoroidal microinjection, or systemic administration.

20. The method of claim 1, wherein the compound is administered to the subject by delivery via oral administration.

21. The method of claim 1, wherein the compound is administered as a pharmaceutical composition comprising the compound and a pharmaceutically acceptable carrier.

22. The method of claim 21, wherein the pharmaceutical composition further comprises a polymer selected from a group consisting of Poly-D,L-Lactic-Co-Glycolic Acid (PLGA), poly-lactic acid (PLA), PLA-PLGA co-polymer, polycaprolactone particles, and chitosan nanoparticles.

23. The method of claim 21, wherein the pharmaceutical composition further comprises Poly-D,L-Lactic-Co-Glycolic Acid (PLGA).

24. The method of claim 22, wherein the pharmaceutical composition is administered to the subject by slow release from a degradable polymeric implant comprising the pharmaceutical composition.

25. The method of claim 21, wherein the pharmaceutical composition is administered to the subject by slow release from an implanted pump device comprising the pharmaceutical composition.

26. The method of claim 9, wherein R is selected from the group consisting of hydrogen, methyl, ethyl, propyl, isopropyl and a cation selected from the group consisting of ammonium, tetra-alkyl ammonium, sodium, potassium, magnesium and zinc.

* * * * *